(12) United States Patent
Yamano et al.

(10) Patent No.: US 8,778,667 B2
(45) Date of Patent: Jul. 15, 2014

(54) METHOD AND UNIT FOR DETECTION OF INTERACTIONS OF BIOLOGICALLY RELEVANT MOLECULES

(75) Inventors: Hirofumi Yamano, Yamaguchi (JP); Shuuichi Kamei, Yamaguchi (JP); Michifumi Tanga, Yamaguchi (JP)

(73) Assignee: Toyo Kohan Co., Ltd., Tokyo (JP)

( * ) Notice: Subject to any disclaimer, the term of this patent is extended or adjusted under 35 U.S.C. 154(b) by 553 days.

(21) Appl. No.: 12/994,990

(22) PCT Filed: May 26, 2009

(86) PCT No.: PCT/JP2009/059931
§ 371 (c)(1),
(2), (4) Date: Nov. 29, 2010

(87) PCT Pub. No.: WO2009/145333
PCT Pub. Date: Dec. 3, 2009

(65) Prior Publication Data
US 2011/0111531 A1 May 12, 2011

(30) Foreign Application Priority Data
May 29, 2008 (JP) ................................ 2008-141155

(51) Int. Cl.
*C12M 1/34* (2006.01)

(52) U.S. Cl.
USPC ... 435/288.1; 435/7.1; 435/283.1; 435/287.1; 435/287.2; 435/288.7

(58) Field of Classification Search
USPC .............. 435/7.1, 283.1, 287.1, 287.2, 288.7, 435/288.1
See application file for complete search history.

(56) References Cited

U.S. PATENT DOCUMENTS

| | | | |
|---|---|---|---|
| 5,418,171 A | 5/1995 | Kimura et al. | |
| 5,578,446 A | 11/1996 | Harris et al. | |

(Continued)

FOREIGN PATENT DOCUMENTS

| | | |
|---|---|---|
| CN | 1617925 A | 5/2005 |
| JP | 10 501069 | 1/1998 |

(Continued)

OTHER PUBLICATIONS

Combined Chinese Office Action and Search Report issued Nov. 14, 2012 in Chinese Patent Application No. 200980119720.7 (with English Translation of Category of Cited Documents).

(Continued)

*Primary Examiner* — Melanie Y Brown
(74) *Attorney, Agent, or Firm* — Oblon, Spivak, McClelland, Maier & Neustadt, L.L.P.

(57) ABSTRACT

The present invention relates to a unit to be used for detection of interactions of biologically relevant molecules using a carrier on which the biologically relevant molecules are immobilized, comprising:
a hollow holder having an open part at one end with the other end being closed; and
a carrier-supporting member that can be inserted into the hollow holder, on which is mounted a carrier upon which biologically relevant molecules are immobilized, wherein:
while the carrier-supporting member is being inserted into the hollow holder, a rear-end portion of the carrier-supporting member is engaged with an edge of the open part of the hollow holder, so that the hollow holder is sealed and the positions of the carrier-supporting member and the hollow holder are determined; and
the area on the left and the area on the right of the axial center, which are defined by the inner side of the hollow holder and the external side of the carrier-supporting member on which the carrier has been mounted, are approximately the same within the region from the carrier-mounting part to the apical part of the carrier-supporting member, as in a section cut along a plane including the axial center of the hollow holder in a positioned state.

7 Claims, 9 Drawing Sheets

(56) References Cited

U.S. PATENT DOCUMENTS

| | | | |
|---|---|---|---|
| 5,772,967 A * | 6/1998 | Wannlund et al. | 422/552 |
| 6,022,700 A * | 2/2000 | Monks et al. | 435/30 |
| 6,396,995 B1 * | 5/2002 | Stuelpnagel et al. | 385/136 |
| 6,905,816 B2 * | 6/2005 | Jacobs et al. | 435/5 |
| 2001/0006417 A1 * | 7/2001 | Modlin et al. | 356/246 |
| 2003/0064386 A1 | 4/2003 | Karaki et al. | |
| 2003/0124029 A1 * | 7/2003 | Webb et al. | 422/102 |
| 2004/0086424 A1 * | 5/2004 | Schembri | 422/58 |
| 2005/0124058 A1 | 6/2005 | Tajima | |

FOREIGN PATENT DOCUMENTS

| | | |
|---|---|---|
| JP | 2003 107083 | 4/2003 |
| JP | 2006 3349 | 1/2006 |
| WO | 92 17782 | 10/1992 |

OTHER PUBLICATIONS

International Search Report issued Aug. 25, 2009 in PCT/JP09/059931 filed May 26, 2009.

* cited by examiner

Fig. 6
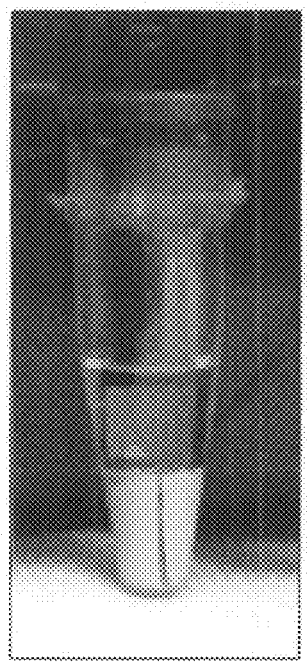
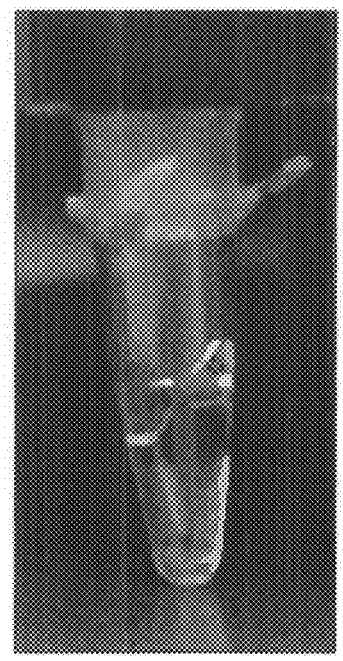

Fig. 8
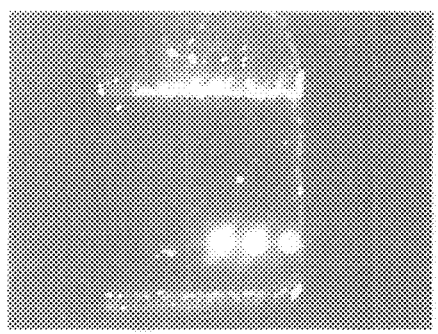 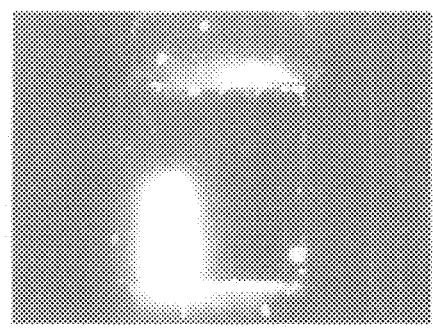

METHOD AND UNIT FOR DETECTION OF INTERACTIONS OF BIOLOGICALLY RELEVANT MOLECULES

CROSS REFERENCE TO RELATED APPLICATIONS

The present application is a 35 U.S.C. §371 national stage patent application of International patent application PCT/JP09/059,931, filed on May 26, 2009, the text of which is incorporated by reference, and claims the benefit of the filing date of Japanese application no. JP 2008-141155, filed on May 29, 2008, the text of which is also being incorporated by reference.

TECHNICAL FIELD

The present invention relates to a method for detection of interactions of biologically relevant molecules using a carrier on which biologically relevant molecules are immobilized and a unit to be used therefor.

BACKGROUND ART

Biologically relevant molecules involved in physiological responses of various organisms have been elucidated as a result of development of genomic analysis. These biologically relevant molecules include DNAs, proteins, sugar chains, and cells, for example. Biologically relevant molecules with functions, structures, and the like that have been elucidated have various industrial applications such as drug development, clinical examination, food inspection, and environmental inspection.

The following methods are generally often employed for examination such as clinical examinations. Specifically, a specimen is brought into contact with a device within which a probe molecule (hereinafter, referred to as "ligand") that specifically binds to a biologically relevant molecule (hereinafter, referred to as "analyte") to be detected has been immobilized on a carrier. When the analyte is present in the specimen, it binds to the ligand and it is then captured on the carrier. Thus, the captured analyte is detected.

Even examination methods described above have required greater speed and automation in recent years. A detection method is now required, by which hundreds to several tens of thousands of biologically relevant molecules can be comprehensively measured simultaneously. Device design using integration technology for immobilization of biologically relevant molecules, namely, MEMS technology, has become possible. A device such as a microarray is used for comprehensive analysis in drug development studies or biological studies.

Examples of microarrays used as devices include, depending on the types of probe molecule to be immobilized on a carrier, DNA microarrays (also referred to as "DNA chip(s)"), protein microarrays (also referred to as "protein chips"), and cell microarrays (also referred to as "cell chip(s)").

Analysis is performed by bringing a specimen labeled in advance with a fluorescent substance into contact with a microarray, washing the microarray, detecting and measuring fluorescence signals emitted by the fluorescent substance, and thus identifying or determining an analyte contained in the specimen (JP Patent Publication (Kohyo) No. 2006-515065 A).

A microarray such as a DNA chip generally has a slide-glass-like size. A specimen is spotted exclusively onto such chip, and then the surface is covered with a preparation for reaction. Automatic mass-processing of microarrays will be required depending on application. In such cases, minituarization of microarrays is desired and development of efficient means for automatically processing the thus miniaturized microarrays is also desired.

SUMMARY OF THE INVENTION

The present inventors have mounted a microarray on a supporting member for automatically processing the miniaturized microarray and then inserted the supporting member into a hollow holder containing a specimen therein for reaction. Thus, they have discovered that since the volume of the specimen is small (ranging from several to hundreds of μ), contact between the specimen and the microarray is insufficient due to the effects of surface tension, resulting in insufficient reaction.

Accordingly, an object of the present invention is to provide a means for sufficiently performing contact between a trace amount of a specimen and a miniaturized microarray upon automatic processing of the microarray.

The present inventors have discovered that contact between the specimen and the microarray can be sufficiently achieved by performing positioning so that the supporting member is inserted into the hollow holder in a nonbiased manner, when a microarray is mounted on a supporting member and then inserted into a hollow holder containing a reaction solution for reaction. Thus, they have completed the present invention.

The present invention encompasses the following.

(1) A unit to be used for detection of an interaction of biologically relevant molecules using a carrier on which the biologically relevant molecules are immobilized, comprising:

a hollow holder having an open part at one end with the other end being closed; and a carrier-supporting member that can be inserted into the hollow holder, on which is mounted a carrier upon which biologically relevant molecules are immobilized wherein:

while the carrier-supporting member is being inserted into the hollow holder, a rear-end portion of the carrier-supporting member is engaged with an edge of the open part of the hollow holder, so that the hollow holder is sealed and the positions of the carrier-supporting member and the hollow holder are determined; and the area on the left and the area on the right of the axial center, which are defined by the inner side of the hollow holder and the external side of the carrier-supporting member on which the carrier has been mounted, are approximately the same within the region from the carrier-mounting part to the apical part of the carrier-supporting member, as in a section cut along a plane including the axial center of the hollow holder in a positioned state.

(2) The unit according to (1), wherein the carrier-mounting part of the carrier-supporting member is a concave portion having a bottom face and side faces and the carrier is disposed on the bottom face of the concave portion.

(3) The unit according to (2), wherein at least the side face on the side of the rear-end portion of the concave portion of the carrier-supporting member is an inclined surface.

(4) The unit according to (3), wherein the surface roughness of the inclined surface is 10 μm or less and the angle formed by the inclined surface and the bottom face is 75° or less.

(5) The unit according to any one of (2) to (4), wherein a waste fluid groove is formed ranging from the side face of the concave portion of the carrier-supporting member, which is closest to the apical part, to the apical part.

(6) The unit according to any one of (1) to (5), wherein the volume of the carrier-supporting member accounts for 60% or more of the volume of the hollow holder within the region from the carrier-mounting part to the apical part of the carrier-supporting member while the carrier-supporting member is being inserted into the hollow holder.

(7) The unit according to any one of (1) to (6), wherein the volume of the carrier-supporting member accounts for 25% to 70% of the volume of the hollow holder while the carrier-supporting member is being inserted into the hollow holder.

(8) The unit according to any one of (1) to (7), comprising a plurality of carrier-supporting members, on each of which a carrier is mounted, the rear-end portions of the carrier-supporting members, each of which is immobilized on the flat member, and a plurality of hollow holders corresponding to each supporting member.

(9) A method for detecting an interaction of biologically relevant molecules using a carrier on which biologically relevant molecules are immobilized, comprising:

an interaction step of causing an interaction of biologically relevant molecules on a carrier with fluorescence-labeled biologically relevant molecules in a reaction solution through insertion of a carrier-supporting member, on which is mounted the carrier upon which biologically relevant molecules are immobilized, into a hollow holder having an open part at one end with the other end being closed and containing the reaction solution;

a washing step of washing the carrier by removing biologically relevant molecules that have not interacted with biologically relevant molecules immobilized on the carrier; and a detection step of using a detector to detect fluorescence via irradiation of the carrier with excitation light, wherein:

while the carrier-supporting member is being inserted into the hollow holder, the rear-end portion of the carrier-supporting member is engaged with the edge of the open part of the hollow holder, so that the hollow holder is sealed and the positions of the carrier-supporting member and the hollow holder are determined; and the area on the left and the area on the right of the axial center, which are defined by the inner side of the hollow holder and the external side of the carrier-supporting member on which the carrier is mounted, are approximately the same within the region from the carrier-mounting part to the apical part of the carrier-supporting member, as in a section cut along a plane including the axial center of the hollow holder in a positioned state.

(10) The method according to (9), wherein the carrier-mounting part of the carrier-supporting member is a concave portion having a bottom face and side faces, wherein the carrier is disposed on the bottom face of the concave portion.

(11) The method according to (10), wherein at least the side face on the side of the rear-end portion of the concave portion of the carrier-supporting member is an inclined surface.

(12) The method according to (11), wherein the surface roughness of the inclined surface is 10 μm or less and the angle formed by the inclined surface and the bottom face is 75° or less.

(13) The method according to any one of (10) to (12), wherein a waste fluid groove is formed ranging from the side face of the concave portion of the carrier-supporting member, which is closest to the apical part, to the apical part.

(14) The method according to any one of (9) to (13), wherein the volume of the carrier-supporting member accounts for 60% or more of the volume of the hollow holder within the region from the carrier-mounting part to the apical part of the carrier-supporting member while the carrier-supporting member is being inserted into the hollow holder.

(15) The method according to any one of (9) to (14), wherein the volume of the carrier-supporting member accounts for 25% to 70% of the volume of the hollow holder while the carrier-supporting member is being inserted into the hollow holder.

(16) The method according to any one of (9) to (15), wherein a carrier is mounted on each of a plurality of carrier-supporting members, the rear-end portions of the carrier-supporting members are each immobilized on a flat member, and each of a plurality of hollow holders corresponds to a supporting member.

According to the present invention, a means for sufficiently bringing a trace amount of specimen into contact with a microarray in automatic processing of the miniaturized microarray.

This description includes part or all of the contents as disclosed in the description and/or drawings of Japanese Patent Application No. 2008-141155, which is a priority document of the present application.

BRIEF DESCRIPTION OF THE DRAWINGS

FIG. 6 shows the results of comparing a case (a) wherein the rear-end portion of a carrier-supporting member is engaged with the edge of open part of a hollow holder with a case (b) of no engagement.
FIG. 8 shows the results of detection using a carrier-supporting member having a waste fluid groove and a carrier-supporting member having no waste fluid groove.

BEST MODES FOR CARRYING OUT THE INVENTION

Figure 1:
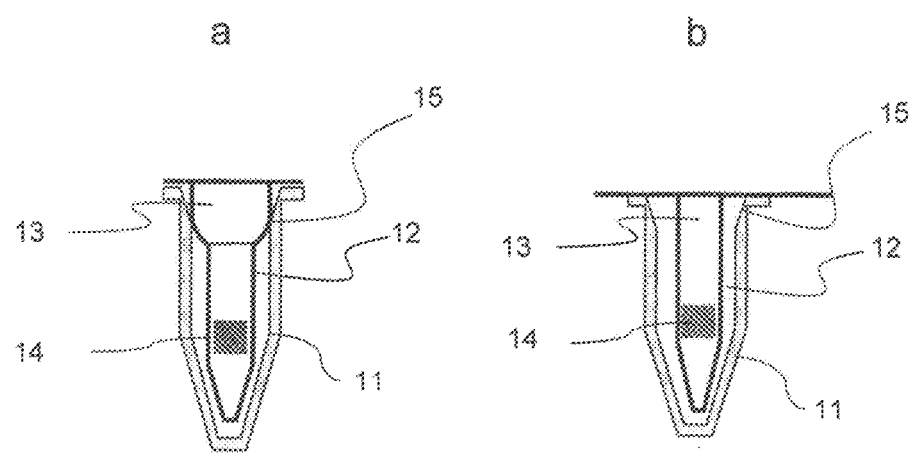
FIG. 1 shows an embodiment of the present invention.

In the present invention, examples of biologically relevant molecules include nucleic acids such as DNA and RNA, peptides, sugar chains, cells, complexes thereof, and complexes of these examples and other molecules. In the present invention, examples of peptides include oligopeptides, polypeptides, and proteins. When biologically relevant molecules to be immobilized on a carrier are peptides, generally a 1-1000 kDa peptide and preferably a 1-200 kDa peptide are preferred. Also, when biologically relevant molecules to be immobilized on a carrier are nucleic acids, generally a nucleic acid of 3-5000 nucleotides and preferably a nucleic acid of 10-1000 nucleotides are preferred. Also when biologically relevant molecules to be immobilized on a carrier are sugar chains, generally a sugar chain of 1-100 sugars and preferably a sugar chain of 1-30 sugars are preferred. In the present invention, a biologically relevant molecule is preferably a nucleic acid and is more preferably DNA.

The term "interaction of biologically relevant molecules" preferably refers to a specific interaction of biologically relevant molecules. Examples of such interaction include a protein-to-protein interaction, a protein-to-peptide interaction, a nucleic acid-to-nucleic acid interaction, a protein-to-nucleic acid interaction, and a protein-to-compound interaction. More specific examples thereof include hybridization between nucleic acid complementary strands, an antigen-antibody reaction or reaction of an antigen with a fragment of an antibody, an enzyme-substrate or enzyme-inhibitor binding reaction, a ligand-receptor binding reaction, a binding reaction between avidin and biotin, a nucleic acid-transcription factor binding reaction, a binding reaction between cell adhesion factors, a sugar chain-protein binding reaction, an aliphatic chain-protein binding reaction, a phosphate group-protein binding reaction, and a cofactor-protein binding reaction.

The present invention is characterized by the use of a unit for detection of an interaction of biologically relevant molecules using a carrier (which may also be referred to as a "microarray") on which biologically relevant molecules have been immobilized. Specifically, the unit comprises: a hollow holder having an open part at one end with the other end being closed; and a carrier-supporting member that can be inserted into the hollow holder, on which a microarray is mounted, whereby
  the carrier-supporting member is inserted into the hollow holder containing a reaction solution to bring the microarray into contact with the reaction solution so as to cause biologically relevant molecules to interact with each other.

The hollow holder having an open part at one end with the other end being closed is not particularly limited, as long as it can contain a reaction solution. Such hollow holder may be an individual holder or form a unit comprised of a plurality of such holders. Examples of such hollow holders include microtubes or microtiter plates (e.g., 96-well plates) that are generally used in the art. The dimensions of such hollow holders can be appropriately set by persons skilled in the art depending on application. For example, a tube-shaped hollow holder having an open part with a diameter ranging from 6 mm to 12 mm and a length ranging from 15 mm to 35 mm can be used herein.

The hollow holder contains as a reaction solution a specimen containing fluorescence-labeled biologically relevant molecules. A carrier-supporting member is inserted into the hollow holder, so as to bring the carrier into contact with the reaction solution and to cause biologically relevant molecules on the carrier to interact with biologically relevant fluorescence-labeled molecules in the reaction solution. A nucleic acid amplification product may also be contained as a reaction solution. In a washing step for washing a carrier to remove biologically relevant molecules that have not interacted with biologically relevant molecules immobilized on the carrier, the hollow holder contains a wash and a carrier-supporting member is inserted into the hollow holder after interaction, so that washing can also be performed. A hollow holder containing a specimen as a reaction solution and a hollow holder containing a wash as a reaction solution can be separately used.

In an interaction step for causing biologically relevant molecules on a carrier to interact with biologically relevant fluorescence-labeled molecules in a reaction solution, the reaction solution is preferably heated by heating the hollow holder. According to the present invention, while a carrier-supporting member is being inserted into a hollow holder, the rear-end portion of the carrier-supporting member is engaged with the edge of the open part of the hollow holder, so that the hollow holder is sealed. Hence, evaporation of the reaction solution can be suppressed while the reaction solution can be simultaneously and efficiently heated. A reaction solution partially evaporated upon heating may form droplets after cooling at the rear-end portion of the carrier-supporting member that seals the hollow holder. Therefore, in the interaction step, the rear-end portion of the carrier-supporting member is also heated to suppress droplet formation, so as to allow prevention of a change in the concentration of biologically relevant molecules in a reaction solution due to a slight decrease in the reaction solution. The heating temperature in the interaction step ranges from 30° C. to 60° C. and preferably ranges from 35° C. to 55° C. This also applies to the heating temperature for the rear-end portion of a carrier-supporting member.

In the present invention, the rear-end portion of a carrier-supporting member is engaged with the edge of the open part of the hollow holder, so that the positions of the carrier-supporting member and the hollow holder are determined, while the carrier-supporting member is being inserted into the hollow holder. For example, as shown in FIG. 1, the rear-end portion 13 of the carrier-supporting member 12 is engaged with the edge 15 of the open part of the hollow holder 11, so that the carrier-supporting member is positioned at a predetermined position within the hollow holder (FIG. 1a). Unless the rear-end portion 13 of the carrier-supporting member 12 is engaged with the edge 15 of the open part of the hollow holder 11, the position of the carrier-supporting member is varied within the hollow holder every time the carrier-supporting member is inserted into the hollow holder. Hence, the carrier-supporting member cannot be positioned as predetermined (FIG. 16).

In the present invention, the carrier-supporting member and the hollow holder are constructed as described above whereby the carrier-supporting member is inserted into the hollow holder, so that the area on the left and the area on the right of the axial center (which are defined by the inner side of the hollow holder and the external side of the carrier-supporting member on which the carrier has been mounted) are approximately the same within the region from the carrier-mounting part to the apical part of the carrier-supporting member, as in a section cut along a plane including the axial center of the hollow holder in the positioned state.

Figure 2:
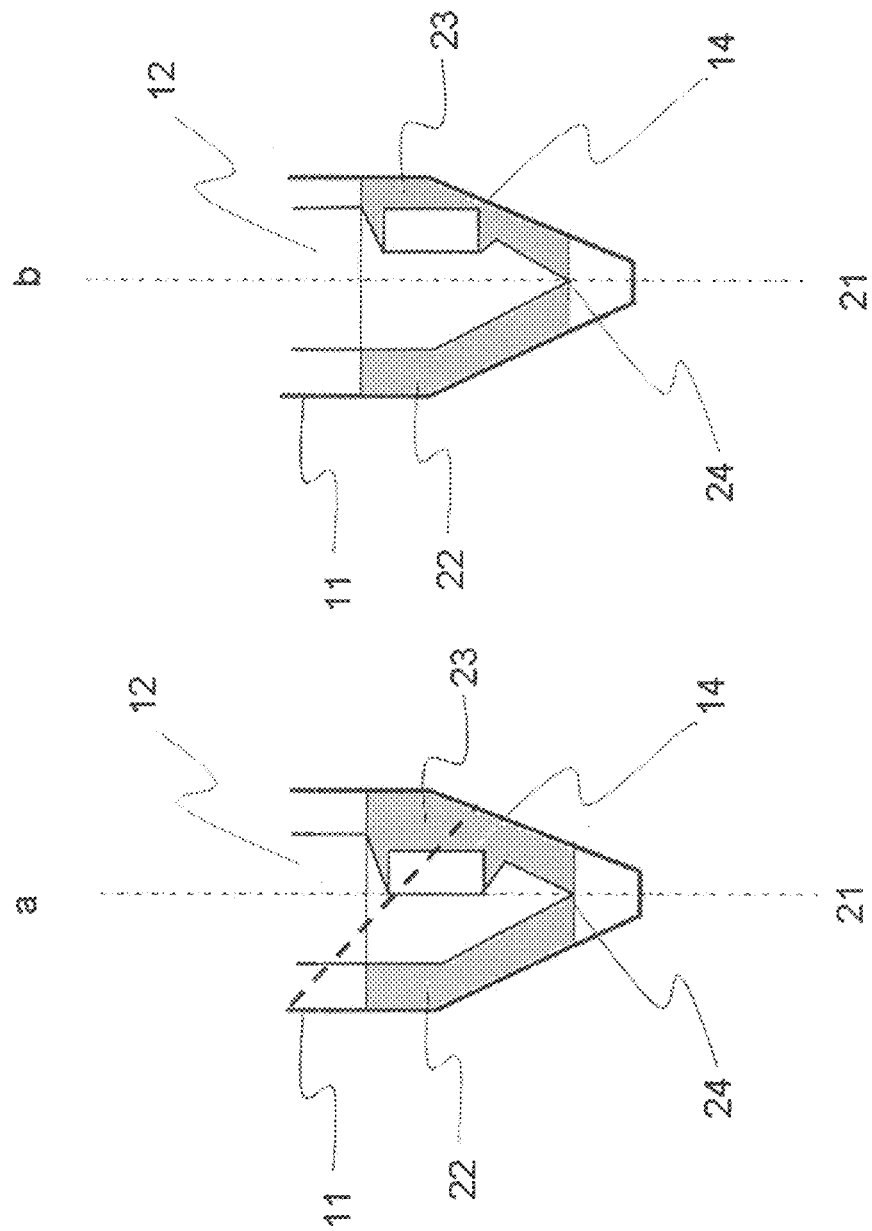
FIG. 2 shows an embodiment of the present invention.

For example, in the above positioned state in which the carrier-supporting member is inserted into the hollow holder, FIG. 2 shows an example of a section cut along a plane including the axial center 21 of the hollow holder. In these sections, regarding areas within the region from the carrier-mounting part of the carrier-supporting member to the apical part 24 (among areas defined by the inner side of the hollow holder and the external side of the carrier-supporting member, on which the carrier has been mounted), the area on the left side of the axial center is the area of the portion represented by 22 and the area on the right side of the axial center is the area of the portion represented by 23. The carrier-supporting member and the hollow holder are constituted so that the area 22 is approximately the same as the area 23. Thus, the surface tension on the left becomes equal to that on the right, and then the carrier 14 can be brought into contact with a reaction solution sufficiently without forming any inclined liquid surface of the reaction solution. In FIG. 2a, the area 22 and the area 23 are not approximately the same, so that the liquid surface of the reaction solution becomes inclined as expressed by the dotted line. On the other hand, in FIG. 2b, the area 22 and the area 23 are approximately the same, and the reaction solution becomes horizontal. The term "approximately the same" refers to a situation in which a difference is 20% or less, preferably 10% or less, and more preferably 5% or less. FIG. 2 shows sections each cut along a plane including the axial center 21 of the hollow holder, wherein particularly the carrier 14 in particular is cut. Therefore, the areas are not symmetric with respect to the axial center of the hollow holder. This similarly applies to a section in which the areas are symmetric with respect to the axial center of the hollow holder. Specifically, the right and the left areas are approximately the same in any sections including the axial center of the hollow holder.

Figure 3:
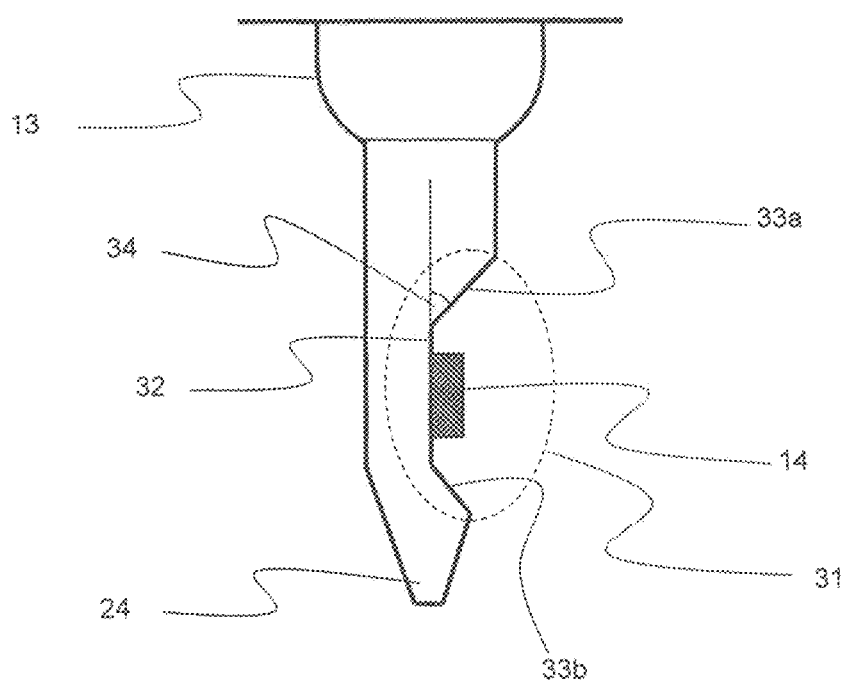
FIG. 3 shows an embodiment of the present invention.

In a preferred embodiment, as shown in FIG. 3, for example, a carrier-mounting part 31 of the carrier-supporting member is a concave portion having a bottom face 32 and side faces 33 (33a and 33b). The carrier 14 is disposed on the bottom face 32 of the concave portion. More preferably, at least the side face 33a on the side of the rear-end portion 13 of the carrier-supporting member concave portion 31 is an inclined surface. The side face 33b on the side of the apical part 24 of the carrier-supporting member concave portion 31 is also preferably an inclined surface. The side face 33a on the side of the rear-end portion is designed to be an inclined surface, so that air bubbles that can be mixed in upon insertion of the carrier-supporting member into a reaction solution within the hollow holder can easily escape to the upper portion. Also, the surface roughness of the inclined surface is determined to be 10 μm or less and is preferably determined to be 1 μm or less and the angle (34 in FIG. 3) formed by the inclined surface and the bottom face is determined to be 75° or less and is preferably determined to be 45° or less, so that air bubbles can escape more easily. Unless air bubbles sufficiently escape, contact between the carrier and the reaction solution is inhibited, and interactions of biologically relevant molecules can be partially inhibited on the carrier. With the above constitution that enables sufficient escape of air bubbles, good contact between the carrier and the reaction solution can be achieved.

Figure 4:
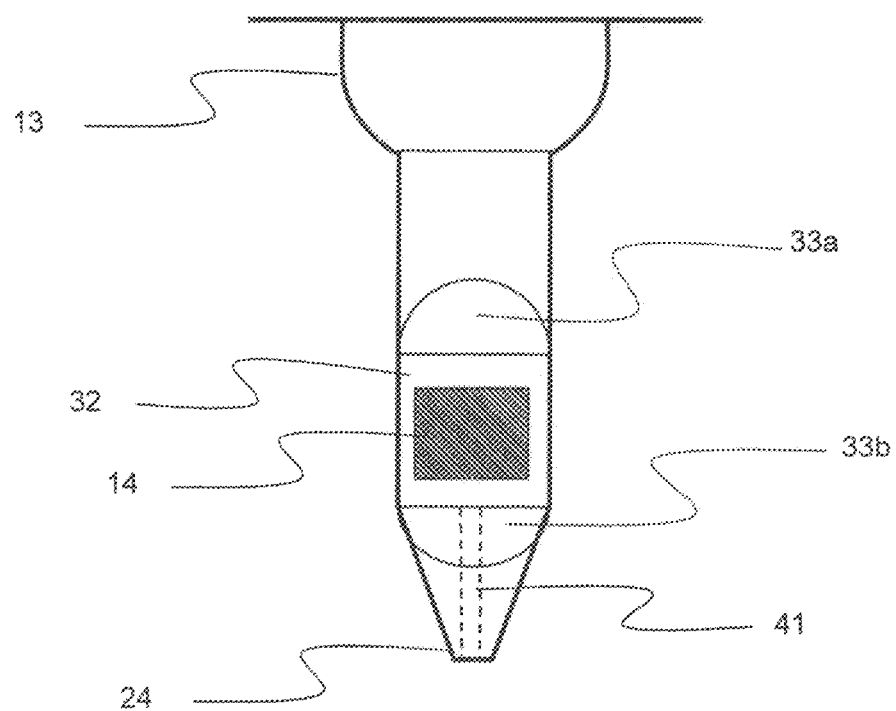
FIG. 4 shows an embodiment of the present invention.

In the carrier-supporting member, a waste fluid groove is preferably formed from the side face of the concave portion, which is closest to the apical part, to the apical part. For example, as shown in FIG. 4, a waste fluid groove 41 is formed from the side face 33b (closest to the apical part) of the concave portion to the apical part 24. Thus, when the carrier-supporting member is removed from a reaction solution within the hollow holder, the reaction solution that can remain in the concave portion can be efficiently discarded. After the carrier-supporting member is removed, the apical part 24 of the carrier-supporting member is brought into contact with filter paper, so that the solution can be more efficiently discarded. According to the present invention, a wash containing a deliquescent substance is used in a washing step for removing biologically relevant molecules that have not interacted with biologically relevant molecules immobilized on the carrier after interaction of biologically relevant molecules, the carrier is directly irradiated with excitation light without becoming dry and then fluorescence can be detected using a detector. A solution containing salt is used for interactions of biologically relevant molecules and washing. When the carrier is dried, irregular drying takes place due to the presence of salt, scattered light is strong due to irregular drying, and accurate detection may be difficult. Particularly in the case of an imaging optical detector, scattered light is strong due to irregular drying and accurate detection may be extremely difficult compared with a case in which a scanning detector is used. Detection is performed without causing drying through the use of a wash containing a deliquescent substance, so that the occurrence of scattered light due to irregular drying can be suppressed. In an embodiment of detection that is performed without causing drying of a carrier, a detection error may arise if a liquid pool is formed in the concave portion of the carrier-supporting member. However, through provision of a waste fluid groove, excess wash remaining in the concave portion can be immediately discarded so that detection errors can be reduced.

A deliquescent substance is not particularly limited, as long as it does not inhibit the interaction of biologically relevant molecules. Examples thereof include alkaline earth metal salts such as magnesium chloride, calcium chloride, and magnesium hydroxide and alkali metal salts such as potassium carbonate and sodium bromide. The concentration of a deliquescent substance in a wash generally ranges from 0.01 mol/l to 3.0 mol/l, preferably ranges from 0.05 mol/l to 1.0 mol/l, and further preferably ranges from 0.2 mol/l to 0.5 mol/l.

Figure 5:
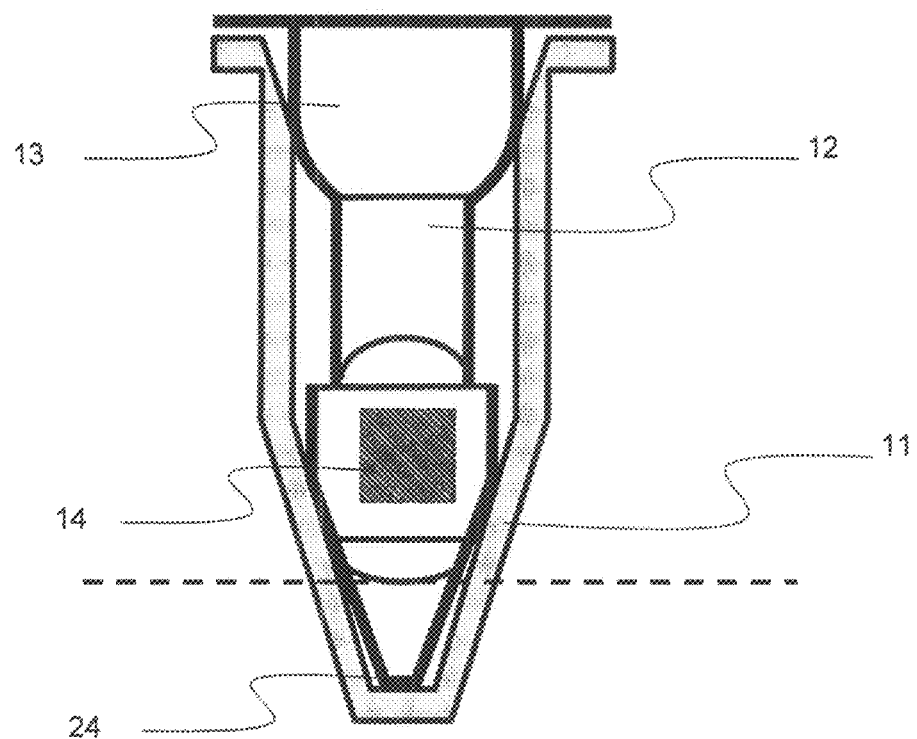
FIG. 5 shows an embodiment of the present invention.

In a preferred embodiment of the present invention, when a carrier-supporting member is inserted into a hollow holder, the volume of the carrier-supporting member accounts for 60% or more, preferably 80% or more, and more preferably 90% to 95% of the volume of the hollow holder within the region from the carrier-mounting part to the apical part 24 of the carrier-supporting member. For example, as shown in FIG. 5, when the carrier-supporting member is inserted in the hollow holder and the hollow holder is cut to give the region (the region below the dotted line) from the carrier-mounting part to the apical part of the carrier-supporting member 12; that is, cut along a plane vertical to the axial center of the hollow holder 11 at the end on the side of the optical part of the carrier-mounting part, the volume of the carrier-supporting member accounts for the percentage of the volume of the hollow holder on the side upon which no carrier-mounting part is mounted is as described above. A portion from the carrier-mounting part of the carrier-supporting member to the apical part is designed to be larger than the other. Therefore, upon insertion of the carrier-supporting member into the hollow holder, even if a trace amount of a reaction solution is contained in the hollow holder, the liquid level is increased so as to enable sufficient contact with the carrier. Accordingly, the amount of the liquid to be used for the procedure can be reduced.

Also, when the carrier-supporting member is inserted in the hollow holder, the volume of carrier-supporting member accounts for preferably 25% to 70% and more preferably accounts for 40% to 50% of the volume of the hollow holder. The volume accounted for the percentage of the volume of the carrier-supporting member is kept to a predetermined level or lower, so as to be able to prevent a liquid from spilling out upon insertion of the carrier-supporting member.

A unit to be used in the present invention may comprise a plurality of carrier-supporting members and a plurality of hollow holders separately corresponding to such supporting members. A carrier is mounted on each of the plurality of carrier-supporting members. Preferably, the rear-end portions of the carrier-supporting members are each mounted on a flat member and they can function in an integrated manner. The expression that "a unit comprises a plurality of hollow holders separately corresponding to carrier-supporting members" refers to a situation in which the unit is constituted so that carrier-supporting members are separately inserted into a plurality of hollow holders. The use of a plurality of carrier-supporting members (on each of which a carrier is mounted)

and a plurality of hollow holders makes it possible to efficiently perform testing for large numbers of samples.

In the detection method of the present invention, after a washing step for washing a carrier so as to remove biologically relevant molecules that have not interacted with biologically relevant molecules immobilized on the carrier, a detection step for irradiating the carrier with excitation light so as to detect fluorescence using a detector is performed.

In the present invention, an imaging optical detector is preferably used as a detector. Use of an imaging optical detector involves irradiating a carrier with excitation light and then detecting the thus obtained fluorescence intensity. Such an imaging optical detector generally comprises a laser for irradiation with excitation light, a fluorescence filter through which only fluorescence of a target wavelength can penetrate, and an optical detection part for detection of fluorescence that has passed through the fluorescence filter (e.g., a CCD camera). Generally in the present invention, the whole carrier is entirely irradiated obliquely with excitation light using a laser in a single instance and then fluorescence is detected from the front face of the carrier. The expression "the carrier is irradiated obliquely with excitation light" refers to a situation in which the angle formed by the carrier surface and laser beam is less than 90°. Generally, irradiation is performed at an angle ranging from 30° to 70° and preferably ranging from 40° to 60°. The imaging optical detector does not require laser scanning over the entire surface of a carrier, and thus detection can be performed within a short time. A carrier is entirely irradiated with excitation light in a single instance. A carrier on which biologically relevant molecules are immobilized has a relatively small size, such as dimensions of 10 mm or less, preferably 5 mm or less, further preferably 3 mm or less, and most preferably 1 mm to 5 mm.

As materials for carriers on which biologically relevant molecules are immobilized, materials known in the art can be used and are not particularly limited. Examples of such materials include: noble metals such as platinum, platinum black, gold, palladium, rhodium, silver, mercury, tungsten, and compounds thereof; conductive materials such as graphite and carbon represented by carbon fiber; silicon materials represented by single crystal silicon, amorphous silicon, silicon carbide, silicon oxide, silicon nitride, and composite materials of such silicon materials, represented by SOI (silicon.on.insulator) and the like; inorganic materials such as glass, quartz glass, alumina, sapphire, ceramics, forsterite, and photosensitive glass; and organic materials such as polyethylene, ethylene, polypropylene, cyclic polyolefin, polyisobutylene, polyethylene terephthalate, unsaturated polyester, fluorine-containing polymer, polyvinyl chloride, polyvinylidene chloride, polyacetic acid vinyl, polyvinyl alcohol, polyvinyl acetal, acrylresin, polyacrylonitrile, polystyrene, acetal resin, polycarbonate, polyamide, phenol resin, urea resin, epoxy resin, melamine resin, styrene.acrylonitrile copolymer, acrylonitrile.butadienestyrene copolymer, polyphenylene oxide, and polysulfone.

In the present invention, preferably a carrier having a carbon layer and a chemical modification group on the surface thereof is used as a carrier. Examples of a carrier having a carbon layer and a chemical modification group on the surface thereof include a carrier having a carbon layer and a chemical modification group on the surface of a substrate and a carrier having a chemical modification group on the surface of a substrate comprising a carbon layer. As materials for such substrate, materials known in the art can be used. Specifically, materials similar to materials used for the above carrier can be used without particular limitation.

The present invention can be preferably used for a carrier having a fine planar structure. A substrate made of a silicon material or a resin material is preferably used, since a carrier having a fine planar structure can be easily produced. In particular, a carrier having a carbon layer and a chemical modification group on the surface of a substrate comprising single crystal silicon is preferably used. Examples of such single crystal silicon include single crystal silicon in which the orientation of the crystallographic axis is slightly and partially varied (which may also be referred to as "mosaic crystal") and single crystal silicon containing atomic scale disorders (lattice defects).

Examples of carbon layers that are preferably used or formed on a substrate include, but are not particularly limited to, surfaces of synthetic diamond, high pressure synthetic diamond, natural diamond, soft diamond (e.g., diamond-like carbon), amorphous carbon, or carbonaceous matter (e.g., graphite, fullerene, and carbon nanotubes), mixtures thereof, or laminated products thereof. Also, carbides such as a hafnium carbide, a niobium carbide, a silicon carbide, a tantalum carbide, a thorium carbide, a titanium carbide, a uranium carbide, a tungsten carbide, a zirconium carbide, a molybdenum carbide, a chrome carbide, and a vanadium carbide can also be used. Here the term "soft diamond" is a generic name used for incomplete diamond structures that are mixtures of diamond and carbon, such as namely Diamond Like Carbon (DLC), and the mixture fractions thereof are not particularly limited. A carbon layer is excellent in chemical stability and is advantageous in that it can withstand the subsequent introduction of a chemical modification group or reaction upon binding with biologically relevant molecules. A carbon layer is also advantageous in that its binding with biologically relevant molecules can take place with flexibility since it can bind via electrostatic binding. A carbon layer is also advantageous in that its binding reaction with biologically relevant molecules results in a low degree of nonspecific adsorption. A carrier wherein a substrate itself comprises a carbon layer can also be used as described above.

In the present invention, a carbon layer can be formed by a known method. Examples of such method include a microwave plasma CVD (chemical vapor deposit) method, an ECRCVD (electric cyclotron resonance chemical vapor deposit) method, an ICP (inductive coupled plasma) method, a direct current sputtering method, an ECR (electric cyclotron resonance) sputtering method, an ionized evaporation method, an arc evaporation method, a laser evaporation method, an EB (electron beam) evaporation method, and a resistance heating evaporation method.

A high-frequency plasma CVD method involves decomposing a raw material gas (methane) by glow discharge generated between electrodes due to high frequency and then synthesizing a DLC (diamond-like carbon) layer on a substrate. An ionized evaporation method involves decomposing and ionizing a raw material gas (benzene) using thermoelectrons generated by tungsten filaments and then forming a carbon layer on a substrate with the use of bias voltage. In a mixed gas comprising a hydrogen gas (1% by volume-99% by volume) with the remainder being methane gas (99% by volume to 1% by volume), a DLC layer may be formed by an ionized evaporation method.

An arc evaporation method involves applying DC voltage between a solid graphite material (cathode evaporation source) and a vacuum vessel (anode) so as to generate arc discharge in a vacuum and generate carbon atom plasma from the cathode and then applying bias voltage (which is more negative than the evaporation source) to the substrate, so as to accelerate the movement of carbon ions in the plasma toward the substrate. Thus, the carbon layer can be formed.

A laser evaporation method involves, for example, irradiating a graphite target plate with Nd:YAG laser (pulsed oscillation) light for melting so as to stack carbon atoms on the glass substrate, thereby forming a carbon layer.

When a carbon layer is formed on the surface of a substrate, the thickness of the carbon layer is generally up to about 100 μm in terms of the monomolecular layer. Excessive thinness thereof may result in the surface of a foundation substrate being locally exposed, but excessive thickness thereof results in poor productivity. Hence, the thickness preferably ranges from 2 nm to 1 μM and more preferably ranges from 5 nm to 500 nm.

Through introduction of a chemical modification group onto the surface of a substrate with a carbon layer formed thereon, biologically relevant molecules can be firmly immobilized on the carrier. A chemical modification group to be introduced can be appropriately selected by persons skilled in the art and is not particularly limited. Examples thereof include an amino group, a carboxyl group, an epoxy group, a formyl group, a hydroxyl group, a metal chelate, and an active ester group.

An amino group can be introduced by subjecting a carbon layer to ultraviolet (UV) irradiation in an ammonia gas or to plasma treatment, for example. Alternatively, an amino group can be introduced by subjecting a carbon layer to UV irradiation in a chlorine gas for chlorination and then further subjecting the same to UV irradiation in an ammonia gas. Alternatively, an amino group can also be introduced by performing a reaction with a chlorinated carbon layer in a polyvalent amine gas such as methylene diamine or ethylene diamine.

A carboxyl group can be introduced by reacting an appropriate compound with the above-aminated carbon layer, for example. Examples of a compound to be used for introduction of a carboxyl group include: halo carboxylic acid represented by the formula: X—$R^1$—COOH (wherein X denotes a halogen atom and $R^1$ denotes a C10-12 divalent hydrocarbon group), such as chloroacetic acid, fluoroacetic acid, bromoacetic acid, iodoacetic acid, 2-chloropropionic acid, 3-chloropropionic acid, 3-chloroacrylic acid, and 4-chlorobenzoic acid; dicarboxylic acid represented by the formula: HOOC—$R^2$—COOH (wherein $R^2$ denotes a single bond or C1-12 divalent hydrocarbon group), such as oxalic acid, malonic acid, succinic acid, maleic acid, fumaric acid, and phthalic acid; polyvalent carboxylic acid such as polyacrylic acid, polymethacrylic acid, trimellitic acid, and butane tetracarboxylic acid; keto acid or aldehyde acid represented by the formula: $R^3$—CO—$R^4$—COOH (wherein $R^3$ denotes a hydrogen atom or C1-12 divalent hydrocarbon group and $R^4$ denotes a C1-12 divalent hydrocarbon group); monohalides of dicarboxylic acid represented by the formula: X—OC—$R^5$—COOH (wherein X denotes a halogen atom and $R^5$ denotes a single bond or C1-12 divalent hydrocarbon group), such as succinic acid monochloride and malonic acid monochloride; and acid anhydrides such as anhydrous phthalic acid, anhydrous succinic acid, anhydrous oxalic acid, anhydrous maleic acid, and anhydrous butane tetracarboxylic acid.

An epoxy group can be introduced by reacting an appropriate polyvalent epoxy compound with the above aminated carbon layer, for example. Alternatively, an epoxy group can be introduced by reacting organic peracid with a carbon=carbon double bond contained in a carbon layer. Examples of organic peracid include peracetic acid, perbenzoic acid, diperoxyphthalic acid, performic acid, and trifluoro peracetic acid.

A formyl group can be introduced by reacting glutaraldehyde with the above-aminated carbon layer, for example.

A hydroxyl group can be introduced by reacting water with the above-chlorinated carbon layer, for example.

The term "active ester group" refers to an ester group having an electron-withdrawing group with high acidity on the alcohol side of an ester group and activating nucleophilic reaction. Such active ester group specifically refers to an ester group with high reaction activity. An active ester group has an electron-withdrawing group on the alcohol side of the ester group, which is activated to a degree higher than alkyl ester. Such active ester group has reactivity to a group such as an amino group, a thiol group, and a hydroxyl group. More specifically, phenol esters, thiophenol esters, N-hydroxyamine esters, cyanomethyl esters, esters of heterocyclic hydroxy compounds, and the like are known as active ester groups having activity much higher than that of alkyl esters and the like. More specifically, examples of such active ester group include a p-nitro phenyl group, an N-hydroxysuccinimide group, a succinimide group, a phthalic imide group, and a 5-norbornene-2,3-dicarboxyimide group. In particular, an N-hydroxysuccinimide group is preferably used.

An active ester group can be introduced by performing active-esterification of the above-introduced carboxyl group using a dehydrating and condensing agent such as cyanamide and carbodiimide (e.g., 1-[3-(dimethylamino)propyl]-3-ethyl carbodiimide) and a compound such as N-hydroxysuccinimide. As a result of this treatment, a group can be formed wherein an active ester group such as an N-hydroxysuccinimide group binds to an end of a hydrocarbon group via amide bond (JP Patent Publication (Kokai) No. 2001-139532).

When nucleic acid such as DNA or RNA is immobilized, an amino group, an epoxy group, a carbodiimide group, a formyl group, or an active ester group is preferably introduced. When a polypeptide is immobilized, an amino group, a carbodiimide group, an epoxy group, a formyl group, a metal chelate, or an active ester group is preferably introduced. With the use of a carrier in which a metal chelate is introduced, a polypeptide having a label that has affinity for metal ions such as a polyhistidine sequence can be effectively and stably immobilized.

A method for immobilizing biologically relevant molecules on the carrier of the present invention is not particularly limited. For example, a solution is prepared by dissolving biologically relevant molecules in a buffer, and then the above-mentioned carrier is immersed in the solution, so that biologically relevant molecules can be immobilized on the surface of the carrier. In general, immersion is performed at 0° C.-98° C. and preferably 4° C.-50° C., for 1 minute to 24 hours and preferably 10 minutes to 1 hour. In such a case, after immersion for a certain period of time, a carrier is washed, so that non-immobilized biologically relevant molecules can be removed. Also, with the use of an apparatus referred to as a spotter, many types of biologically relevant molecules can be immobilized on the surface of a carrier. When a spotter is used, for example, a solution of biologically relevant molecules is spotted onto a carrier using a spotter, baking is performed for a predetermined time period in a heated oven, and then non-immobilized molecules are removed by washing. With the use of such a spotter apparatus, many types of biologically relevant molecules can be immobilized at different positions on a carrier, so that many tests can be conducted at once.

EXAMPLES

Hereafter, the present invention is described in greater detail with reference to the examples, although the technical scope of the present invention is not limited thereto.

Example 1

Carrier-supporting members shown in FIG. 1a and FIG. 1b were inserted into hollow holders containing a reaction solution. The results are shown separately in FIG. 6a and FIG. 6b. In FIG. 6a, the rear-end portion of the carrier-supporting member was engaged with the edge of the open part of the hollow holder so that the position of the carrier-supporting member was determined to be inserted into the central part of the hollow holder. As a result, the liquid surface of the reaction solution was horizontal and the carrier was in contact with the reaction solution. In FIG. 6b, the rear-end portion of the carrier-supporting member was not engaged with the edge of the open part of the hollow holder, so that the carrier-supporting member was inserted while being bent to the right side within the hollow holder. As a result, the liquid surface of the reaction solution inclined due to surface tension, resulting in areas in which the carrier was not in contact with the reaction solution.

Example 2

A membrane of double DLC layers was produced on a 3-mm silicon substrate under the following conditions using an ionized evaporation method.

|  |  | 1st layer | 2nd layer |  |
|---|---|---|---|---|
| Raw material gas | $CH_4$ | 4.75 | 47.5 | (sscm) |
|  | $H_2$ | 0.25 | 2.5 | (sscm) |
| Working pressure |  | 3.0 | 8.0 | (Pa) |
| Substrate bias | DC voltage | 500 | 500 | (V) |
|  | High-frequency output | 100 | — | (W) |
| Anode voltage |  | 50 | 50 | (V) |
| Filament | Voltage | 7 | 7 | (V) |
|  | Current | 22 | 22 | (A) |

An amino group was introduced onto the surface of the thus obtained silicon substrate having DLC layers under the following conditions using ammonia plasma.

|  |  |  |  |
|---|---|---|---|
| Raw material gas | $NH_3$ | 30 | (sscm) |
| Working pressure |  | 8.0 | (sscm) |
| Substrate bias | DC voltage | 500 | (Pa) |
|  | High-frequency output | — | (W) |
| Anode voltage |  | 50 | (V) |
| Filament | Voltage | 7 | (V) |
|  | Current | 22 | (A) |

The resultant was immersed in a 1-methyl-2-pyrrolidone solution containing 140 mM anhydrous succinic acid and 0.1 M sodium borate for 30 minutes, and then a carboxyl group was introduced. Activation was performed via 30 minutes of immersion in a solution containing 0.1M potassium phosphate buffer, 0.1 M 1-[3-(dimethylamino)propyl]-3-ethyl carbodiimide, and 20 mM N-hydroxysuccinimide. Thus, a carrier was obtained comprising DLC layers and a N-hydroxysuccinimide group as a chemical modification group on the surface of the silicon substrate.

Figure 7:
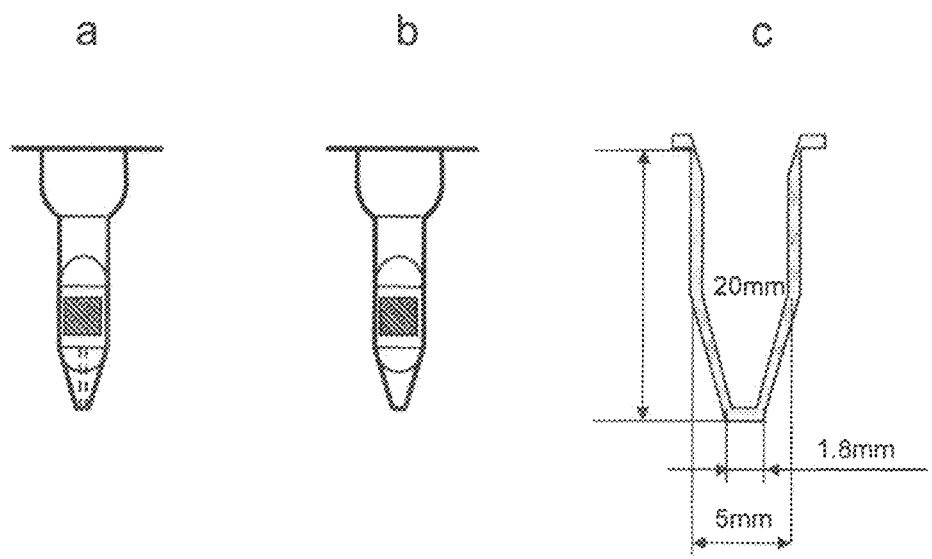
FIG. 7 shows an embodiment of (a) a carrier-supporting member having a waste fluid groove, (b) a carrier-supporting member having no waste fluid groove, and (c) a hollow holder.

A DNA probe was dissolved in Sol.6 (Toyo Kohan Co., Ltd.) to 10 μM and then the solution was spotted onto the carrier. After 1 hour of baking at 80° C. followed by washing with 2×SSC/0.2% SDS, washing with ultrapure water and then centrifugal drying were performed. Thus, the DNA probe was immobilized on the carrier. A region hybridizing to the above probe was amplified by PCR. Labeling was performed using CyDye. The composition of a PCR solution was as follows. The thus obtained PCR product (30 μl) was dissolved in 30 μl of a hybridization solution (4×SSC/0.2% SDS solution), thereby preparing a sample. The sample (50 μl) was added to a hollow holder shown in FIG. 7c. Carriers on each of which the above-obtained DNA probe had been immobilized were each mounted on carrier-supporting members shown in FIG. 7a and FIG. 7b and then the carrier-supporting members were separately inserted into hollow holders containing the sample. The carrier-supporting member shown in FIG. 7a had a waste fluid groove, but the carrier-supporting member shown in FIG. 7b had no waste fluid groove. After insertion of the carrier-supporting members, 2 minutes of reaction was performed at 55° C., and then washing was performed once with 2×SSC/0.2% SDS, once with 1 N sodium acetate/0.5% Tween 20, and then once with 1 N $MgCl_2$/0.5% Tween 20. With the use of a cooled CCD camera, fluorescent labels of biologically relevant molecules that had interacted on the carriers were detected via a fluorescence filter (for Cy5, Edmund Optics). The carrier surfaces were irradiated with excitation light at an angle of 50° with respect to the surface using a φ5-mm laser (640-nm wavelength). FIG. 8 shows the results.

When a carrier-supporting member (FIG. 7a) having a waste fluid groove had been used, no liquid pool was formed on the carrier-mounting part, and detection could be successfully performed (FIG. 8a). On the other hand, when a carrier-supporting member (FIG. 7b) having no waste fluid groove had been used, liquid pools were observed in some cases (FIG. 8b).

Example 3

Figure 9:
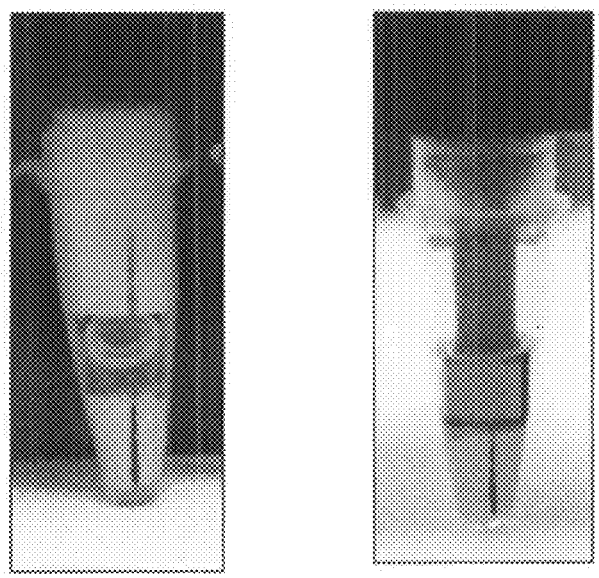
FIG. 9 shows the results of inserting (a) a carrier-supporting member wherein the volume thereof accounts for 80% of the volume of a hollow holder into a hollow holder containing a reaction solution and (b) a carrier-supporting member wherein the volume thereof accounts for 50% of the volume of a hollow holder into the same, when each carrier-supporting member is inserted into a hollow holder.

While being inserted into the hollow holders, a carrier-supporting member (FIG. 9a) characterized in that the volume thereof accounts for 80% of the volume of the hollow holder and a carrier-supporting member (FIG. 9b) characterized in that the volume thereof accounts for 50% of the same were separately inserted into hollow holders containing a reaction solution. In FIG. 9a, air bubbles were formed upon insertion. As demonstrated in FIG. 9b, no air bubbles were formed upon insertion and that contact between the reaction solution and the carrier was satisfactory.

All publications, patents, and patent applications cited herein are incorporated herein by reference in their entirety.

DESCRIPTION OF REFERENCE NUMERALS

11: hollow holder, 12: carrier-supporting member, 13: rear-end portion of carrier-supporting member, 14: carrier, 15: open part of the hollow holder, 21: hollow holder axial center, 24: apical part of carrier-supporting member, 31: carrier-mounting part, 32: bottom face of carrier-mounting part, 33: side face (inclined surface) of carrier-mounting part, 34: angle formed by bottom face and side face (inclined surface), and 41: waste fluid groove

The invention claimed is:

1. A method for detecting an interaction of at least one first biologically relevant molecule with a carrier on which at least one second biologically relevant molecule is immobilized, the method comprising:
  (A) causing an interaction of the at least one second biologically relevant molecule on the carrier with the at least one first biologically relevant molecule, which has been fluorescence-labeled, in a reaction solution through insertion of a carrier-supporting member, on which is mounted the carrier upon which the at least one second biologically relevant molecule is immobilized, into a hollow holder having an open part at one end with a second end being closed and comprising the reaction solution;
  (B) washing the carrier by removing biologically relevant molecules that have not interacted with the at least one second biologically relevant molecule immobilized on the carrier; and
  (C) detecting fluorescence via irradiation of the carrier with excitation light with a detector, wherein:
  while the carrier-supporting member is being inserted into the hollow holder, a rear-end portion of the carrier-supporting member is engaged with an edge of the open part of the hollow holder, so that the hollow holder is sealed and positions of the carrier-supporting member and the hollow holder are determined;
  a left area, left of an axial center of the hollow holder, and a right area, right of the axial center of the hollow holder, which are defined by an inner side of the hollow holder and an external side of the carrier-supporting member on which the carrier is mounted, are approximately the same within a region from a carrier-mounting part to an apical part of the carrier-supporting member, as in a section cut along a plane including the axial center of the hollow holder in a positioned state;
  the carrier-mounting part is disposed on a surface between a rear-end of the carrier-supporting member and the apical part of the carrier-supporting member; and
  the carrier-mounting part of the carrier-supporting member is a concave portion having a bottom face and side faces, and the carrier is disposed on the bottom face of the concave portion.

2. The method according to claim 1, wherein at least a side face on the side of the rear-end portion of the concave portion of the carrier-supporting member is an inclined surface.

3. The method according to claim 2, wherein a surface roughness of the inclined surface is 10 μm or less and an angle formed by the inclined surface and the bottom face is 75° or less.

4. The method according to claim 1, wherein a waste fluid groove is formed ranging from a side face of the concave portion of the carrier-supporting member, which is closest to the apical part, to the apical part.

5. The method according to claim 1, wherein a volume of the carrier-supporting member accounts for 60% or more of a volume of the hollow holder within the region from the carrier-mounting part to the apical part of the carrier-supporting member while the carrier-supporting member is being inserted into the hollow holder.

6. The method according to claim 1, wherein a volume of the carrier-supporting member accounts for 25% to 70% of a volume of the hollow holder while the carrier-supporting member is being inserted into the hollow holder.

7. The method according to claim 1, wherein a carrier is mounted on each of a plurality of carrier-supporting members, rear-end portions of the carrier-supporting members are each immobilized on a flat member, and each of a plurality of hollow holders corresponds to a supporting member.

* * * * *